(12) United States Patent
Miyako et al.

(10) Patent No.: US 7,897,933 B2
(45) Date of Patent: Mar. 1, 2011

(54) RADIATION IMAGE CAPTURING APPARATUS

(75) Inventors: Kuniaki Miyako, Minami-ashigara (JP); Hajime Nakata, Minami-ashigara (JP); Kazuo Hakamata, Odawara (JP); Yasunori Ohta, Yokohama (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 12/234,413

(22) Filed: Sep. 19, 2008

(65) Prior Publication Data

US 2009/0080620 A1    Mar. 26, 2009

(30) Foreign Application Priority Data

Sep. 21, 2007    (JP) .................................. 2007-245326

(51) Int. Cl.
*G01T 1/24* (2006.01)
*H01J 35/10* (2006.01)

(52) U.S. Cl. .................................. 250/370.15; 378/199

(58) Field of Classification Search ............. 250/370.15, 250/370.01, 370.08, 370.09; 378/37, 199
See application file for complete search history.

(56) References Cited

U.S. PATENT DOCUMENTS

| 6,268,614 | B1 | 7/2001 | Imai | |
| 6,573,640 | B1* | 6/2003 | Hakamata et al. | 313/39 |
| 6,818,885 | B2* | 11/2004 | Negi et al. | 250/239 |
| 7,511,277 | B2* | 3/2009 | Ueno et al. | 250/363.08 |
| 2004/0228450 | A1* | 11/2004 | Mueller | 378/199 |
| 2005/0287008 | A1* | 12/2005 | Lacey et al. | 417/32 |
| 2006/0126782 | A1* | 6/2006 | Pohan et al. | 378/19 |

FOREIGN PATENT DOCUMENTS

JP    2000-037374 A    2/2000

* cited by examiner

*Primary Examiner* — David P Porta
*Assistant Examiner* — Faye Boosalis
(74) *Attorney, Agent, or Firm* — Sughrue Mion, PLLC

(57) ABSTRACT

A radiation image capturing apparatus includes a cooling mechanism for causing cooling medium to flow from a rear surface side to a radiation detector to a front surface side of radiation detector through a narrow space formed between an end of the radiation detector and a casing for housing the radiation detector. It is therefore possible to cool the narrow space, as well as regions in the vicinity of the narrow space, with the cooling medium and to discharge the cooling medium from the front surface side of the radiation detector.

15 Claims, 6 Drawing Sheets

US 7,897,933 B2

RADIATION IMAGE CAPTURING APPARATUS

CROSS-REFERENCE TO RELATED APPLICATION

This application relates to and claims priority to Japanese Patent Application number 2007-245326, filed on Sep. 21, 2007 the entire disclosure of which is incorporated herein by reference.

BACKGROUND OF THE INVENTION

1. Field of the Invention

The present invention relates to a radiation image capturing apparatus including a radiation detector for sensing a radiation image of a subject and outputting the radiation image as an electrical signal. More specifically, the present invention relates to a radiation image capturing apparatus including a cooling mechanism for cooling the radiation detector.

2. Description of the Related Art

In a radiation image capturing apparatus such as an X-ray breast image capturing apparatus (e.g., a mammography apparatus) or the like, a radiation image is generated by exposing a subject (patient) to radiation, and the radiation image is recorded into a radiation image recording unit (i.e., a radiation detector). Information corresponding to the radiation image is then read out by causing a reading light source to move relative to the radiation image recorder for applying a reading light. An example of such a radiation image capturing apparatus is disclosed in U.S. Pat. No. 6,268,614.

Examples of radiation image recording units that can be used in the aforementioned apparatus include a radiation detector of electric readout type having a plurality of photoelectric conversion elements and devices such as thin-film transistors (TFT), CCD (Charge Coupled Device) or CMOS (Complimentary Metal Oxide Semiconductor) sensor, along with light readout type, direct conversion type, or indirect conversion type radiation detectors.

In these types of radiation image capturing apparatus, a proper temperature range must be maintained due to constraints resulting from temperature characteristics of the photoelectric conversion elements, the effects of thermal noise generated in the electric circuits, and the like. Therefore, such radiation image capturing apparatus have been provided with an air cooler or a water cooler therein. One example of such an apparatus is disclosed in Japanese Laid-Open Patent Publication No. 2000-037374.

Japanese Laid-Open Patent Publication No. 2000-037374 is directed to effective cooling of the radiation detector. As can be seen in FIG. 1 of the aforementioned publication, the radiation image capturing apparatus includes a two-dimensional radiation detector 5 and a signal converter 6, which are contained within a casing 4 of an image capturing unit 3, in this order from the front of the casing 4. A fan 7, which forms a cooling unit, is provided in an upper portion of the casing 4, and an inlet port 4a for introducing outside air is provided in a lower portion of the casing 4. Release of heat, which is generated by the two-dimensional radiation detector 5, can be carried out by actuating the fan 7, and thereby introducing air into the casing 4 through the inlet port 4a.

In the apparatus disclosed in Japanese Laid-Open Patent Publication No. 2000-037374, the inlet port 4a is formed at one end of the radiation detector 5, while the fan 7 is located at the other end thereof, so that cooling of the entire radiation detector 5 can be achieved. In many types of radiation image capturing apparatuses, however, the arrangement of the radiation detector within the image capturing unit is restricted due to various reasons. In a mammography apparatus, for instance, it is necessary to capture images from various directions by moving the image capturing unit. The dimensions of the casing of the image capturing unit are therefore restricted, and the radiation detector has to be contained within a small space inside the casing. Moreover, because the mamographic image must include the base of the breast of the patient, the distance between the radiation detector and the chest wall of the patient has to be kept extremely short. Hence, in mammography apparatus, the radiation detector is located close to a side of the casing that abuts against the chest wall, thus making it difficult to release a sufficient amount of heat generated in the narrow space between the radiation detector and the side of the casing. This results in non-uniform cooling of the radiation detector, which in turn tends to cause imaging accuracy to deteriorate.

SUMMARY OF THE INVENTION

It is an object of the invention to provide a radiation image capturing apparatus that allows uniform cooling of a radiation detector, irrespective of constraints on the arrangement of the radiation detector within a casing.

The radiation image capturing apparatus according to the present invention includes a radiation detector for detecting a radiation image of a subject and outputting the radiation image as an electrical signal, a casing for housing the radiation detector, and a cooling mechanism for causing a cooling medium to flow from a rear surface side to a front surface side of the radiation detector through a narrow space formed between the casing and one end of the radiation detector.

According to the present invention, the cooling medium is caused to flow from the rear surface side to the front surface side of the radiation detector through the narrow space formed between one end of the radiation detector and the casing. It is therefore possible to cool the narrow space, as well as regions in the vicinity of the narrow space, with the cooling medium and to discharge the cooling medium from the front surface side of the radiation detector. Consequently, the entire detection surface of the radiation detector can be cooled in a uniform manner.

The cooling mechanism may further include a fan, which enables a reliable flow of the cooling medium from the rear surface side of the radiation detector to the front surface side thereof to be achieved.

Further, the fan may be provided on an upstream side of a duct disposed on the rear surface side of the radiation detector. The radiation image capturing apparatus may preferably include a guiding device for guiding the cooling medium from the fan to the duct. Such an arrangement causes the cooling medium to flow more reliably into the duct that is disposed on the rear side surface of the radiation detector. As a result, the arrangement enables an improvement in the cooling efficiency of the radiation detector.

The above and other objects, features, and advantages of the present invention will become more apparent from the following description when taken in conjunction with the accompanying drawings in which a preferred embodiment of the present invention is shown by way of illustrative example.

DESCRIPTION OF THE PREFERRED EMBODIMENTS

Figure 1:
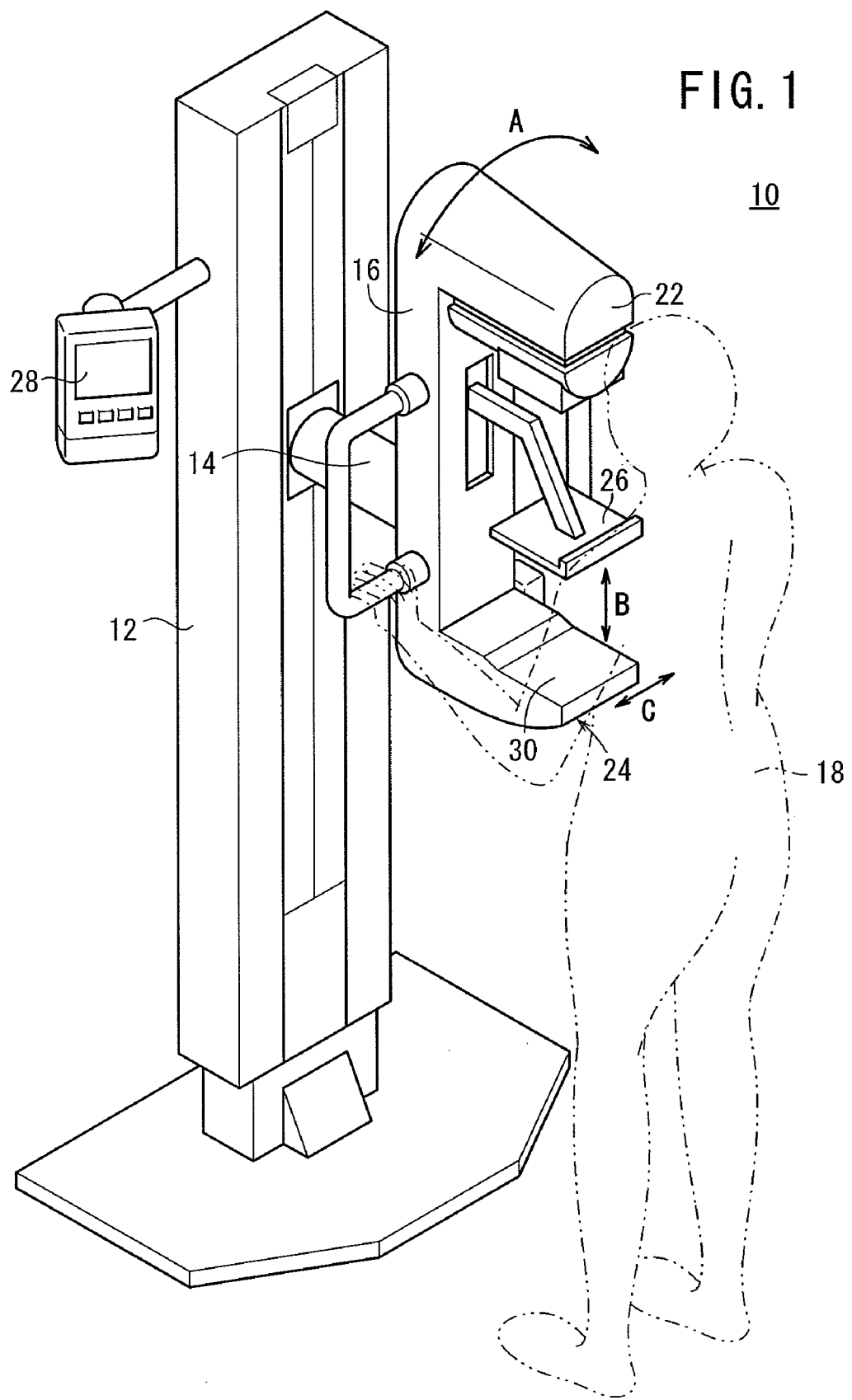
FIG. 1 is a perspective view of a mammography apparatus forming a radiation image capturing apparatus according to an embodiment of the present invention.

FIG. 1 is a perspective view of an embodiment of a radiation image capturing apparatus according to the present invention, which makes up a mammography apparatus 10 used for breast cancer screening and the like.

The mammography apparatus 10 includes an upstanding base 12, an arm 16 fixed to a pivot shaft 14 that is connected substantially centrally to the base 12, a radiation source housing unit 22 fixed to one end of the arm 16 and housing a radiation source (not shown) therein for applying radiation X, or other types of electromagnetic waves for recording, to a breast 20 (see FIG. 2) of the subject 18 which is to be imaged, an image capturing base 24 fixed to the other end of the arm 16 in opposition to the radiation source housing unit 22, and a compression plate 26 for holding the breast 20 by compressing the breast 20 against the image capturing base 24.

The arm 16 holding the radiation source housing unit 22 and the image capturing base 24 can be rotated about the pivot shaft 14 in the directions indicated by the double-headed arrow A to adjust the image capturing direction with respect to the breast 20 of the subject 18. The compression plate 26 is connected to the arm 16 between the radiation source housing unit 22 and the image capturing base 24 so as to be movable in the directions shown by the double-headed arrow B.

The base 12 also is provided with a display control unit 28 for displaying image capturing information of the image obtained by the mammography apparatus 10 along with identification information (ID) or the like of the subject 18. The image capturing information includes the image capturing site, the image capturing direction, etc., for the image of the subject 18 to be captured by the mammography apparatus 10.

Figure 2:
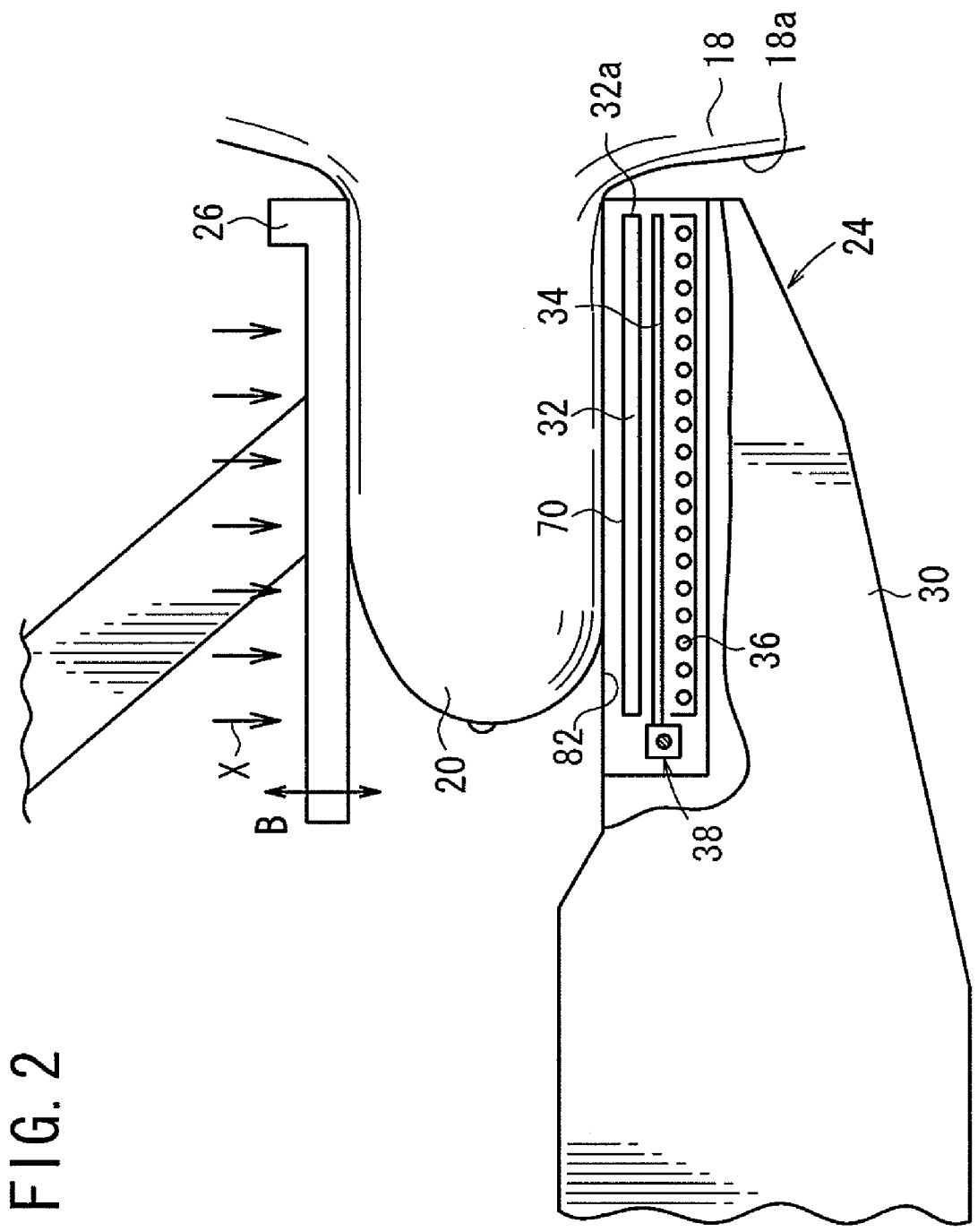
FIG. 2 is a partial cross-sectional side view showing an internal structure of the image capturing base in the mammography apparatus of FIG. 1.
Figure 3:
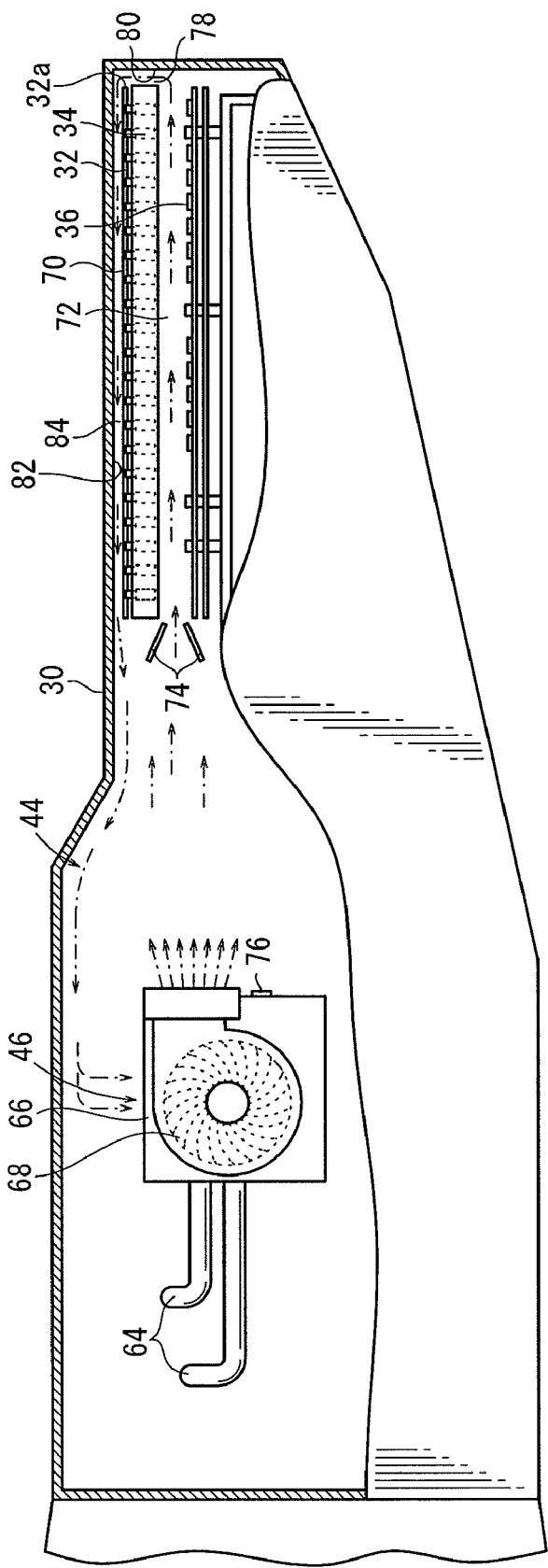
FIG. 3 is a detailed view of a portion of the image capturing base shown in FIG. 2.

FIG. 2 is a partial cross-sectional side view showing an internal structure of the image capturing base 24 in the mammography apparatus 10. FIG. 2 shows the image capture site on the subject 18, which is the breast 20, placed between the image capturing base 24 and the compression plate 26. FIG. 3 shows a portion of the image capturing base 24 in greater detail.

As shown in FIG. 3, the casing 30 of the image capturing base 24 contains a planar radiation detector 32. The radiation detector 32 stores radiation image information, which is captured based on the radiation X emitted from the radiation source in the radiation source housing unit 22, and outputs the radiation image information as electric signals. The casing 30 also contains a reading light source 34 that applies a linear reading light to the radiation detector 32 in order to read out the radiation image information recorded therein, and an erasing light source 36 that applies an erasing light to the radiation detector 32. The reading light source 34 is scanned by a scanning mechanism 38 (see FIG. 2) over the radiation detector 32 in directions perpendicular to the plane of FIG. 3 (the directions indicated by the double-headed arrow C in FIG. 1).

Figure 4:
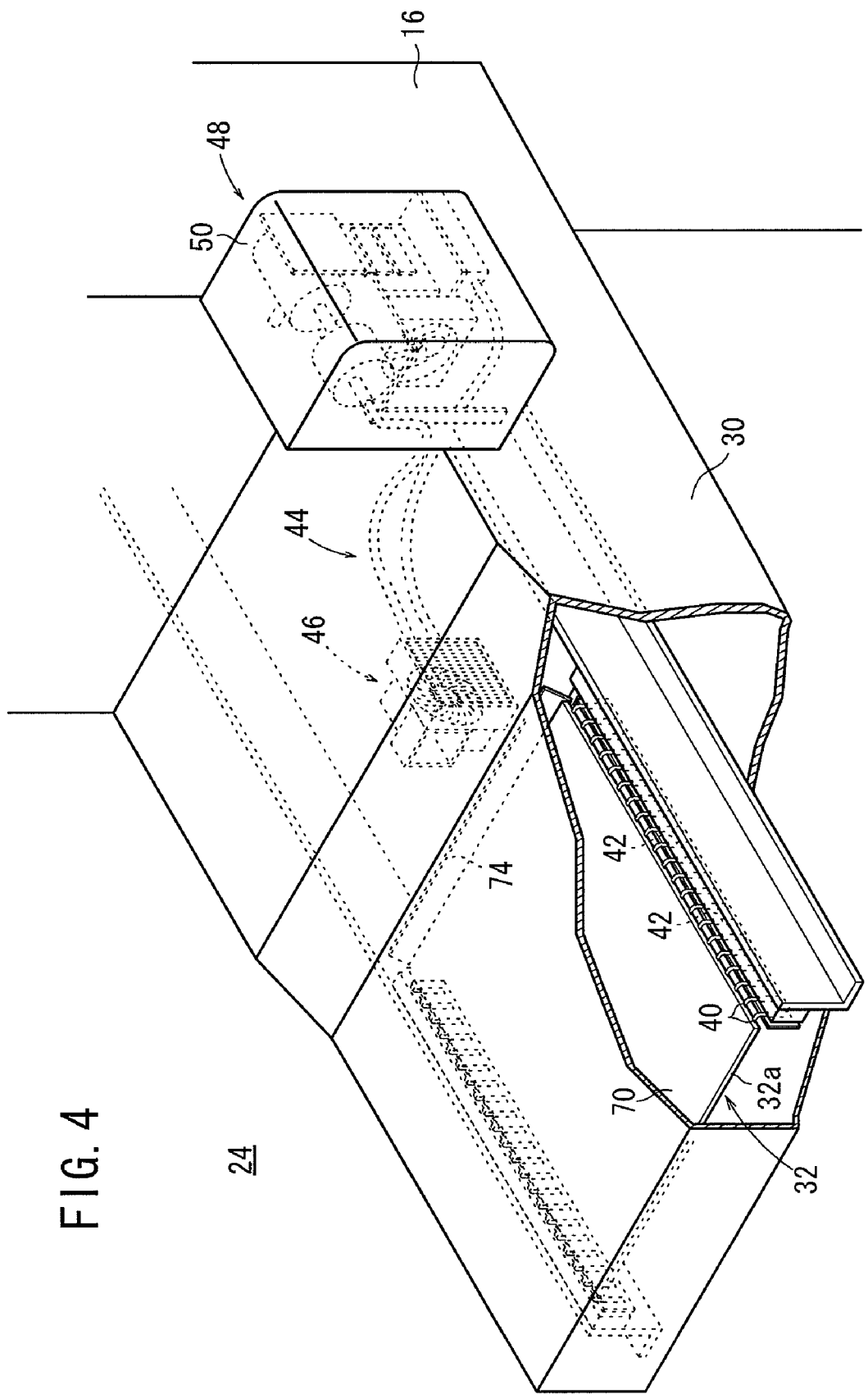
FIG. 4 is a partially cutaway perspective view of the image capturing base including a radiation detector and a temperature control mechanism.
Figure 5:
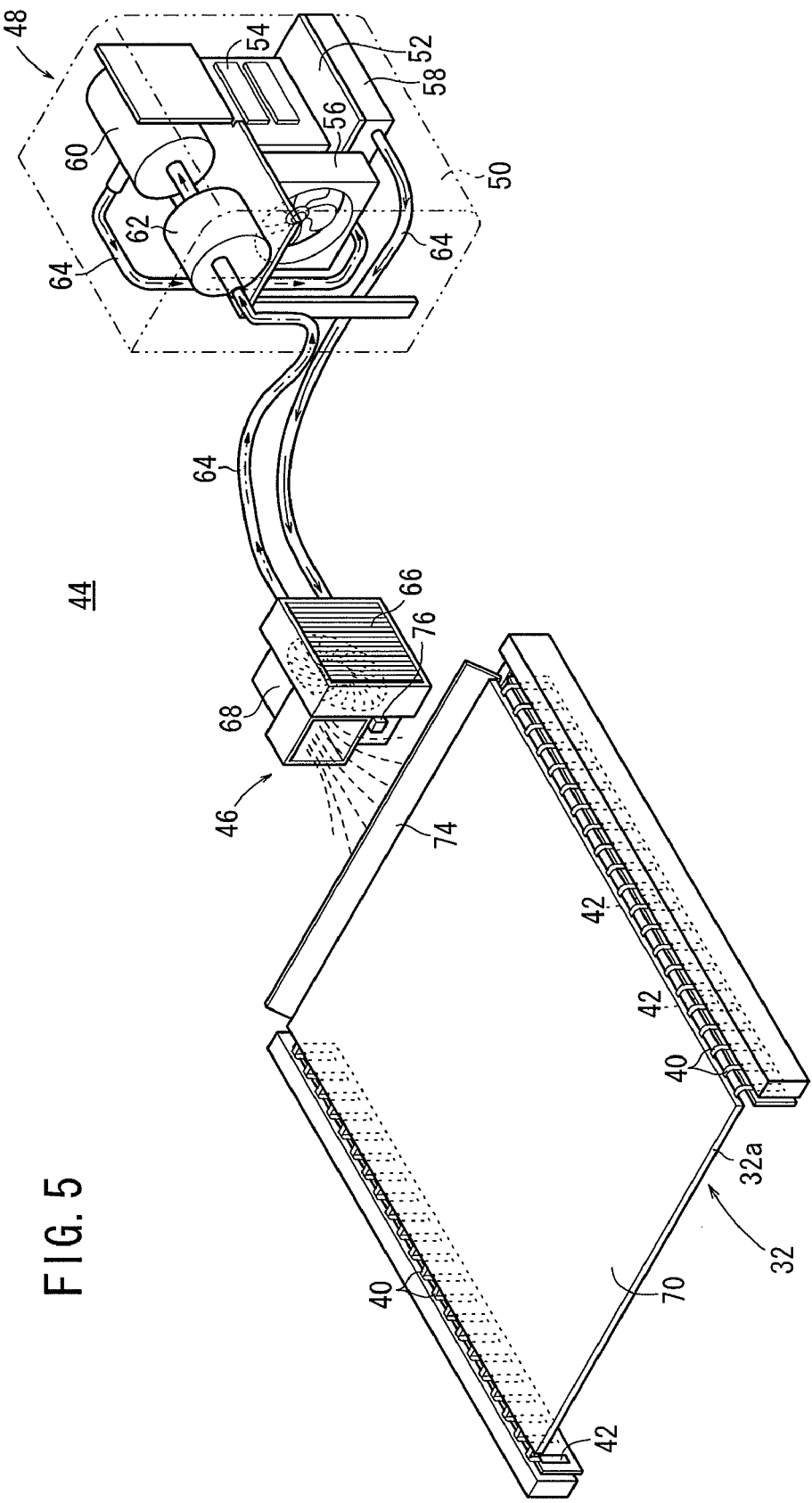
FIG. 5 is an internal perspective view of the radiation detector and the temperature control mechanism.

As shown in FIGS. 4 and 5, linear electrodes of the radiation detector 32 are each connected to a flexible substrate 40. Each flexible substrate 40 is provided with an ASIC (Application Specific Integrated Circuit) 42 such as an amplifier in proximity to the linear electrode. The flexible substrates 40 are connected to various other substrates via an A/D converter. The casing 30 is provided with a temperature controlling mechanism 44, which is capable of keeping the temperature in the casing 30 at or below the outside air temperature.

The radiation detector 32 is a direct-conversion, light readout type solid-state detector. The radiation detector stores radiation image information produced based on the radiation X that has passed through the breast 20 as an electrostatic latent image. Further, when scanned by the reading light from the reading light source 34, the radiation detector 32 generates an electric current corresponding to electric charges of the electrostatic latent image. An example of a radiation detector that may be utilized in the present embodiment is disclosed in U.S. Pat. No. 6,268,614.

As shown in FIGS. 3 to 5, the temperature controlling mechanism 44 includes a cooling air supply unit 46, which supplies cooling air at least to the radiation detector 32, and a coolant supply unit 48 which supplies a coolant, such as an LLC (Long Life Coolant), to the cooling air supply unit 46.

The coolant supply unit 48 is equipped with a casing 50, which is disposed with respect to the arm 16 in proximity to the pivot shaft 14. As shown in FIG. 5, the casing 50 houses a Peltier element 52 integrated with heat sinks 54 and a Peltier fan 56. A water-cooled jacket 58 is installed on the Peltier element 52. A water circulating pump 60 and a receiver tank 62 are provided above the heat sinks 54 and the Peltier fan 56.

The cooling air supply unit 46 includes a radiator 66 provided within the casing 30, a sirocco fan 68 connected to the radiator 66, and a louver 74 for guiding cooled air supplied from the sirocco fan 68 to a duct 72 (see FIG. 3) formed on a rear surface side (i.e., the side opposing the detection surface 70) of the radiation detector 32. The coolant supplied from the water-cooled jacket 58 of the coolant supply unit 48 is supplied to the radiator 66 through a circulating pipe 64. The coolant supplied to the radiator 66 is returned to the receiver tank 62 through the circulating pipe 64.

As shown in FIGS. 3 and 5, a temperature sensor 76 is installed on the radiator 66 in proximity to a cooling air nozzle of the sirocco fan 68. The temperature sensor 76 detects the ambient temperature of the air around the radiation detector 32 by detecting the temperature within the casing 30.

Operation of the mammography apparatus 10 according to the present embodiment having the above configuration shall now be described.

First, ID information concerning the subject 18, image capturing conditions, and the like are supplied to the mammography apparatus 10 by means of a console (not shown), an ID card, or the like. The ID information may include information concerning the name, age, gender, etc., of the subject 18, and such information can be acquired from an ID card of the subject 18. If the mammography apparatus 10 is connected to a network, the ID information may also be acquired from other apparatuses connected to the network. The image capturing conditions may include an image capturing site, an image capturing direction, or the like, as specified by the physician. Such items of information may also be acquired from a higher-level apparatus on the network, or entered through the console by a radiologist. The ID information, image capturing conditions, and the like may be displayed on the display control unit 28 of the mammography apparatus 10 for purposes of verification.

The radiologist then sets the mammography apparatus 10 in accordance with specified image capturing conditions. The image capturing directions of the breast 20 may include, for example, a craniocaudal view (CC), a mediolateral view (ML), and a mediolateral oblique view (MLO), in which image capturing is performed by exposing the breast 20 to x-rays from the top, side, and an oblique angle, respectively. The arm 16 is rotated about the pivot shaft 14 in accordance with the specified image capturing direction.

Next, the breast 20 of the subject 18 is positioned with respect to the mammography apparatus 10, i.e., the breast 20 is placed on the image capturing base 24 and the compression plate 26 is moved down to hold the breast 20 between the image capturing base 24 and the compression plate 26 (see FIG. 2).

After the above preparatory operations have been completed, the radiation source (not shown) in the radiation source housing unit 22 is activated to expose the breast 20 to radiation X in accordance with preset image capturing conditions. Radiation X that has passed through the breast 20 negatively charges the radiation detector 32, thereby forming a latent image. Negative charging of the radiation detector 32 may be achieved in accordance with the method disclosed in U.S. Pat. No. 6,268,614, for example.

After the latent image has been recorded in the radiation detector 32, the reading light source 34 is moved by the scanning mechanism 38 (see FIG. 2) in at least one of the directions indicated by the double-headed arrow C of FIG. 1 (auxiliary direction) in order to scan the reading light emitted from the reading light source 34 over the radiation detector 32, thereby allowing a processing circuit (not shown) to read out the radiation image information from the radiation detector 32. For further details concerning such readout processing, refer to the aforementioned U.S. Pat. No. 6,268,614, which discloses the applicable processing.

During recording and readout of the radiation image information from the radiation detector 32, heat is generated by the radiation detector 32 and other devices arranged within the casing 30 of the image capturing base 24. The heat accumulates and the temperature inside the casing 30 rises, increasing the risk of abnormal operation of the radiation detector 32. As already mentioned, the space 78, which is formed between the radiation detector 32 and the side surface 80 (see FIG. 3) on the side of the casing 30 that abuts against the chest wall 18a of the subject 18, is narrow, thus making it difficult for the generated heat to be released. In the present embodiment, however, cooling of the interior space of the casing 30, and in particular the aforementioned narrow space 78, can be achieved in the following manner.

Specifically, the sirocco fan 68 is operated with the radiator 66 in a functioning state. With this arrangement, cooled air (cooling medium) is supplied to the duct 72 on the rear surface side of the radiation detector 32 from the sirocco fan 68 via the louver 74. The supplied air then hits the side surface 80 on the chest wall 18a side of the casing 30, and passes along the side surface 80 to the detection surface 70 side of the radiation detector 32. The air then moves toward the pivot shaft 14, between the detection surface 70 of the radiation detector 32 and a surface 82 of the casing 30 that opposes the detection surface 70. With this arrangement, heat that has accumulated in the narrow space 78 formed between the end 32a of the radiation detector 32 and the side surface 80 of the casing 30, and heat that has accumulated in the narrow space 84 between the detection surface 70 of the radiation detector 32 and the surface 82 of the casing 30, is displaced toward the pivot shaft 14, thereby enabling cooling of the radiation detector 32.

Air that has moved toward the pivot shaft 14 is cooled by the radiator 66 upon each circulation thereof, and the air is supplied to the radiation detector 32 via the sirocco fan 68 and the louver 74.

As described above, the mammography apparatus 10 of the present invention includes the cooling air supply unit 46, which causes cooled air to flow to a front surface side (side on which the detection surface 70 is located) of the radiation detector 32 from a rear surface side of the radiation detector 32, and through a narrow space 78 between the end 32a of the radiation detector 32 and the side surface 80 of the casing 30.

According to the above-described embodiment, the narrow space 78 and nearby regions can be cooled by the cooled air, and air can be released from the front surface side of the radiation detector 32. It therefore is possible to cool the entire detection surface 70 of the radiation detector 32 in a uniform manner.

The cooling air supply unit 46 includes the sirocco fan 68 for causing the cooled air to flow. By use of the sirocco fan 68, it is possible to obtain a reliable flow of cooled air from the rear surface side to the front surface side of the radiation detector 32.

Moreover, the sirocco fan 68 is provided on an upstream side of the duct 72, which is disposed on the rear surface side of the radiation detector 32, while the mammography apparatus 10 further includes the louver 74 for guiding the cooled air from the sirocco fan 68 to the duct 72. This arrangement allows the cooled air to be reliably delivered to the duct 72, and consequently enables an improvement in the cooling efficiency of the radiation detector 32.

The present invention is not limited to the aforementioned embodiment. Various changes and modifications may be made in light of the description herein, without departing from the scope of the appended claims. For example, the invention can make use of any of the following forms.

The radiation image capturing apparatus is not limited to use with a mammography apparatus 10, as in the above-described embodiment. The radiation image capturing apparatus may comprise a radiation image capturing apparatus that employs an electronic cassette or another type of radiation image capturing apparatus.

In the above embodiments, the light readout type radiation detector 32 is used, and however, the radiation detector 32 is not limited to such a light readout type radiation detector. An electric readout type radiation detector may be used, such as a radiation detector having TFTs of a-Si on a glass substrate, a radiation detector having organic TFTs on a resin substrate, or a radiation detector having CCD (Charge Coupled Device) or CMOS (Complementary Metal Oxide Semiconductor) sensors on a silicon substrate.

Instead of a direct-conversion, light readout type radiation detector 32 as used in the embodiment described above, a radiation detector of the indirect conversion type may be employed that includes a scintillator for temporarily converting radiation X into visible light, together with a photoconductive recording layer that generates electrical charge pairs when exposed to the visible light. Alternatively, a radiation detector of the electric readout type may be utilized.

Although a sirocco fan 68 is employed in the above-described embodiment, a propeller fan, or another type of fan may also be used.

Although the above-described radiation detector 32 is provided in the sealed casing 30 and air is circulated inside the casing 30, the present invention is not limited to this configuration.

Figures 6A, 6B:
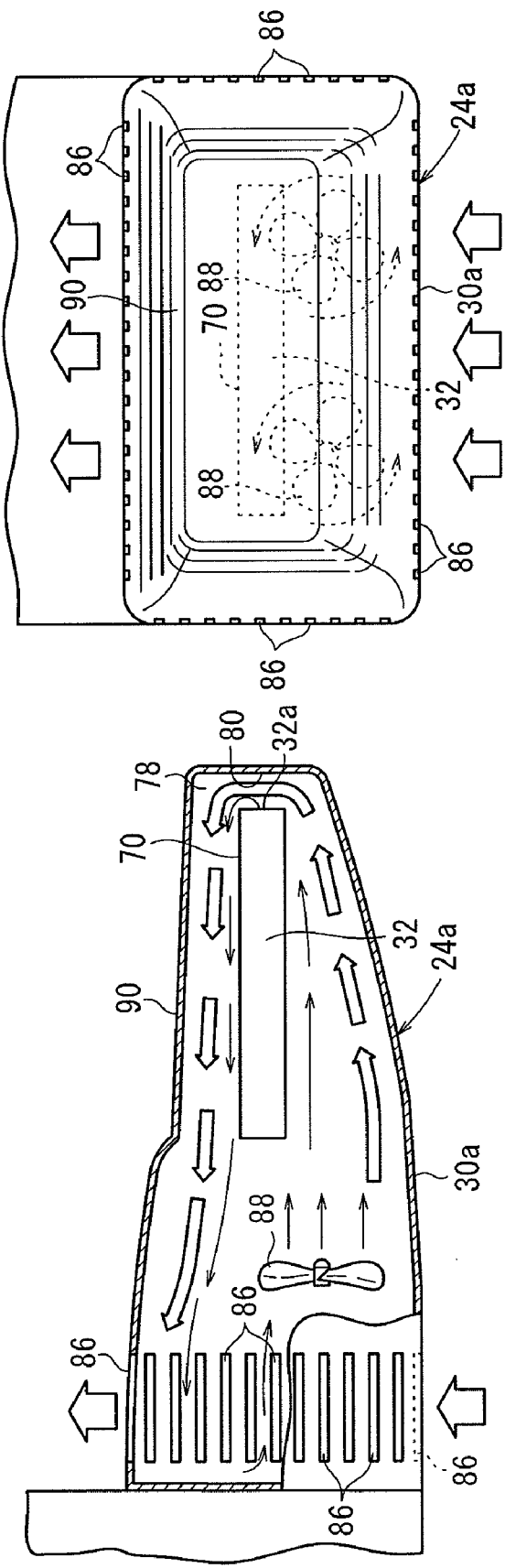
FIG. 6A is a cross-sectional side view of a first modification of the image capturing base, showing the airflow therein.
FIG. 6B is a front view of the first modification of the image capturing base, showing the airflow therein.

For instance, as shown in FIGS. 6A and 6B, an image capturing base 24a may be used in which the radiation detector 32 is cooled using outside air. FIG. 6A is a cross-sectional side view of the image capturing base 24a, and FIG. 6B is a front view of the image capturing base 24a. The image capturing base 24a includes a casing 30a having a plurality of slits 86 formed at intervals around the external circumference of the image capturing base 24a on the side of the pivot shaft 14 (shown on the left in FIG. 6A), and a fan 88 for causing air to flow within the casing 30a. Outside air is sucked into the casing 30a through the slits 86 positioned at a lower part of the casing 30a, and the air is forced to flow over the radiation detector 32 using the fan 88, thereby cooling the radiation detector 32.

The casing 30a includes an inclined surface 90, which is inclined so that the casing 30a widens between the side that abuts against the chest wall 18a of the subject 18 (right side in FIG. 6A) toward the side of the pivot shaft 14 (left side in FIG. 6A). Thus, as a result of being lighter than the outside air, relatively high temperature air (i.e., air having a higher temperature than the outside air) that exists within the narrow space 78 between the end 32a of the radiation detector 32 and the side surface 80 on the chest wall 18a side of the casing 30a moves (upwardly) along the inclined surface 90 toward the pivot shaft 14, even if the fan 88 is not operating.

Note that FIGS. 6A and 6B show a simplified view of the radiation detector 32. Other constituent elements, such as the reading light source 34 and the erasing light source 36, have been omitted from illustration.

It should be noted, in the above-described embodiment, although the louver 74 is used to guide the cooled air to the duct 72, the present invention may employ another guiding device. A configuration without a guiding device also is possible.

What is claimed is:

1. A radiation image capturing apparatus comprising:
   a radiation detector for detecting a radiation image of a subject and outputting the radiation image as an electrical signal;
   a casing for housing the radiation detector; and
   a cooling mechanism for causing a cooling medium to flow from a rear surface side of the radiation detector to a front surface side of the radiation detector through a narrow space formed between an end of the radiation detector and the casing.

2. The radiation image capturing apparatus according to claim 1, wherein the cooling mechanism includes a fan for causing the cooling medium to flow.

3. The radiation image capturing apparatus according to claim 2, further comprising:
   a duct provided on the rear surface side of the radiation detector, the fan being provided on an upstream side of the duct; and
   a guiding device for guiding the cooling medium from the fan into the duct.

4. The apparatus of claim 1, wherein the casing includes slits for venting the cooling medium.

5. The apparatus of claim 4, wherein the cooling medium is air.

6. The apparatus of claim 1, wherein the casing further houses a coolant circulating device for cooling the cooling medium.

7. The apparatus of claim 1, wherein the cooling mechanism causes the cooling medium to flow along the rear surface side and the front surface side of the radiation detector.

8. The apparatus of claim 7, further comprising a louver that directs the cooling medium along the rear surface side of the radiation detector.

9. The apparatus of claim 1, wherein the cooling mechanism causes the cooling medium to flow in a first direction along the rear surface side of the radiation detector, through the narrow space, and in a second direction along the front side surface of the radiation detector, the first direction being opposite to the second direction.

10. The apparatus of claim 9, wherein the cooling medium flows in a continuous flow path.

11. A radiation image capturing apparatus comprising:
    a radiation detector for detecting a radiation image of a subject and outputting the radiation image as an electrical signal;
    a casing for housing the radiation detector; and
    a cooling mechanism for causing a cooling medium to flow from one surface of the radiation detector to another surface of the radiation detector through a narrow space formed between an end of the radiation detector and the casing.

12. The apparatus of claim 11, wherein the cooling mechanism causes the cooling medium to flow along the one surface of the radiation detector and the another surface of the radiation detector.

13. The apparatus of claim 12, further comprising a louver that directs the cooling medium along the rear surface side of the radiation detector.

14. The apparatus of claim 11, wherein the cooling mechanism causes the cooling medium to flow in a first direction along the rear surface side of the radiation detector, through the narrow space, and in a second direction along the front side surface of the radiation detector, the first direction being opposite to the second direction.

15. The apparatus of claim 14, wherein the cooling medium flows in a continuous flow path.

* * * * *